US011401357B2

(12) United States Patent
Hama et al.

(10) Patent No.: US 11,401,357 B2
(45) Date of Patent: Aug. 2, 2022

(54) WATER-ABSORBENT RESIN AND ABSORBENT ARTICLE

(71) Applicant: SUMITOMO SEIKA CHEMICALS CO., LTD., Hyogo (JP)

(72) Inventors: Maoki Hama, Himeji (JP); Kenta Kumazawa, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 291 days.

(21) Appl. No.: 16/754,976

(22) PCT Filed: Oct. 12, 2018

(86) PCT No.: PCT/JP2018/038102
§ 371 (c)(1),
(2) Date: Apr. 9, 2020

(87) PCT Pub. No.: WO2019/074099
PCT Pub. Date: Apr. 18, 2019

(65) Prior Publication Data
US 2020/0299423 A1  Sep. 24, 2020

(30) Foreign Application Priority Data

Oct. 12, 2017  (JP) .............................. JP2017-198261

(51) Int. Cl.
| | |
|---|---|
| *C08F 20/06* | (2006.01) |
| *B01J 20/26* | (2006.01) |
| *C08F 2/18* | (2006.01) |
| *C08F 22/06* | (2006.01) |
| *C08F 210/02* | (2006.01) |
| *C08F 210/06* | (2006.01) |
| *C08K 5/00* | (2006.01) |
| *C08K 5/1515* | (2006.01) |

(52) U.S. Cl.
CPC ............. *C08F 20/06* (2013.01); *B01J 20/267* (2013.01); *C08F 2/18* (2013.01); *C08F 22/06* (2013.01); *C08F 210/02* (2013.01); *C08F 210/06* (2013.01); *C08K 5/0025* (2013.01); *C08K 5/1515* (2013.01); *C08F 2438/01* (2013.01); *C08F 2810/00* (2013.01)

(58) Field of Classification Search
CPC .... A61K 31/4745; A61K 47/58; A61K 47/32; C08F 220/365; C08F 220/606; C08F 297/00; C08F 220/603; A61P 35/00; B01J 20/28002
See application file for complete search history.

(56) References Cited

U.S. PATENT DOCUMENTS

| | | | | |
|---|---|---|---|---|
| 5,306,867 A | * | 4/1994 | Connole | H01B 7/285 174/230 |
| 2007/0093766 A1 | * | 4/2007 | Yoshino | A61F 13/531 604/368 |
| 2008/0280154 A1 | | 11/2008 | Kobushi et al. | |
| 2012/0295103 A1 | * | 11/2012 | Kikuno | C08F 6/008 524/732 |
| 2016/0030919 A1 | * | 2/2016 | Hinayama | A61L 15/60 525/384 |
| 2017/0107313 A1 | | 4/2017 | Murakami et al. | |
| 2017/0210831 A1 | | 7/2017 | Hinayama et al. | |
| 2018/0215993 A1 | | 8/2018 | Sakamoto et al. | |
| 2019/0105628 A1 | | 4/2019 | Kotake et al. | |

FOREIGN PATENT DOCUMENTS

| | | | |
|---|---|---|---|
| EP | 2 130 581 A1 | | 12/2009 |
| EP | 2 893 974 A1 | | 7/2015 |
| JP | H05-247307 | * | 9/1993 |
| JP | H05-247307 A | | 9/1993 |
| JP | 2000-084533 A | | 3/2000 |
| JP | 2003-088552 A | | 3/2003 |
| JP | 2005-334616 A | | 12/2005 |
| JP | 2006-176570 A | | 7/2006 |
| JP | 2006-289154 A | | 10/2006 |
| JP | 2016-28131 A | | 2/2016 |
| WO | 03/106513 A1 | | 12/2003 |
| WO | 2006/123561 A1 | | 11/2006 |
| WO | 2011/065368 A1 | | 6/2011 |

(Continued)

OTHER PUBLICATIONS

Translation of JPH05-247307 (Year: 1993).*
Third party observations dated Feb. 10, 2022 from the European Patent Office in European Application No. 18866231.6.
Third Party Observation Communication for PCT/JP2018/038102 dated Feb. 3, 2020.
International Search Report for PCT/JP2018/038102 dated Dec. 25, 2018 (PCT/ISA/210).
Kato, Shinjiro, "High water absorbing resin", Sanyo Kasei news, 2010, New Year No. 48 (5 pages total).
Office Action dated May 10, 2022 from the Japanese Patent Office in JP Application No. 2019-548257.

*Primary Examiner* — Robert C Boyle
(74) *Attorney, Agent, or Firm* — Sughrue Mion, PLLC

(57) ABSTRACT

Provided are a water-absorbent resin easily separable from a recyclable resource in recovering the recyclable resource, and an absorbent article containing an absorbent material containing the water-absorbent resin. The water-absorbent resin according to the present invention has such a structure that a polymer formed from a water-soluble ethylenically unsaturated monomer is crosslinked by using a post-crosslinking agent. The water-absorbent resin has (1) a water-retention capacity for physiological saline of 35 g/g or more, (2) a water-absorption capacity for physiological saline under a load of 4.14 kPa of 10 mL/g or more, (3) an initial gel viscosity of 3000 mPa·s or more, and (4) a gel decomposition index of 0.60 or less: gel decomposition index=B/A wherein A represents an initial gel viscosity (mPa·s), and B represents a gel viscosity after one day (mPa·s).

4 Claims, 1 Drawing Sheet

(56) References Cited

FOREIGN PATENT DOCUMENTS

| WO | 2016/006129 A1 | 1/2016 |
| WO | 2016/006133 A1 | 1/2016 |
| WO | 2016/006135 A1 | 1/2016 |
| WO | 2017/017964 A1 | 2/2017 |
| WO | 2017/169246 A1 | 10/2017 |

* cited by examiner

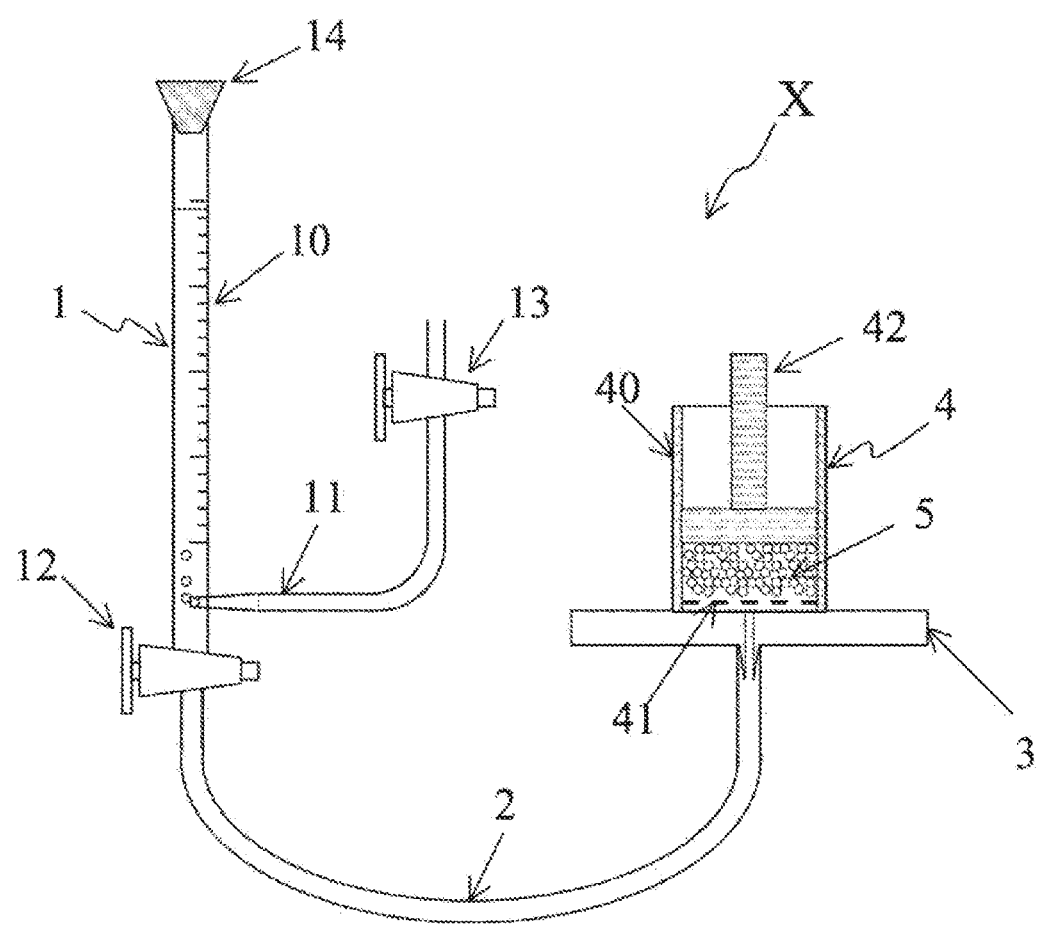

WATER-ABSORBENT RESIN AND ABSORBENT ARTICLE

CROSS REFERENCE TO RELATED APPLICATIONS

This application is a National Stage of International Application No. PCT/JP2018/038102 filed Oct. 12, 2018, claiming priority based on Japanese Patent Application No. 2017-198261 filed Oct. 12, 2017.

TECHNICAL FIELD

The present invention relates to a water-absorbent resin and an absorbent article.

BACKGROUND ART

Water-absorbent resins have a wide range of applications in a variety of fields, including for hygiene materials, such as disposable diapers and sanitary products, agriculture and horticulture materials, such as water retention agents and soil conditioners, and industrial materials, such as waterproof agents and dew-resistant agents. In particular, water-absorbent resins are often used in hygiene materials such as disposable diapers, sanitary products, and portable toilets.

From the standpoint of environmental protection, attempts have been made to recover and reuse a recyclable resource (e.g., pulp) contained in used hygiene materials (e.g., disposable diapers). To recover a recyclable resource from a hygiene material, the recyclable resource must be first separated from a water-absorbent resin. In general, however, a water-absorbent resin that has absorbed water and turned into a gel ("used water-absorbent resin") is difficult to separate from the recyclable resource; thus, it is difficult to recover only the recyclable resource, excluding the used water-absorbent resin, from the hygiene material.

To solve this problem, a method has been studied in which a used water-absorbent resin is first decomposed, and then a recyclable resource is recovered. For example, in PTL 1 and 2, used disposable diapers are torn apart, and then a used water-absorbent resin contained in disposable diapers is decomposed into monomers using water mixed with a polymer decomposer, followed by separating and recovering a pulp component, which is a recyclable resource.

CITATION LIST

Patent Literature

PTL 1: JP2000-084533A
PTL 2: JP2006-289154A

SUMMARY OF INVENTION

Technical Problem

However, because the decomposition of a used water-absorbent resin in PTL 1 and 2 requires a polymer decomposer, not only does the recovery operation for the recyclable resource become cumbersome, but also a stock of the polymer decomposer must always be kept.

The present invention was made in view of these problems, and an object of the invention is to provide a water-absorbent resin easily separable from a recyclable resource in recovering the recyclable resource, and to provide an absorbent article comprising an absorbent material that contains the water-absorbent resin.

Solution to Problem

The present inventors found that the use of a water-absorbent resin that exhibits excellent self-decomposing properties after having absorbed water enables separation of a used water-absorbent resin from a recyclable resource in a simple manner, without relying on an external means, such as a polymer decomposer. After having conducted extensive research, the inventors completed a water-absorbent resin according to the present invention.

Specifically, the present inventors conducted extensive research on a water-absorbent resin that exhibits excellent self-decomposing properties after having absorbed water. Consequently, the inventors found that when a water-absorbent resin that has such a structure that a polymer formed from a water-soluble ethylenically unsaturated monomer is crosslinked by using a post-crosslinking agent satisfies specific physical properties, a water-absorbent resin that exhibits excellent self-decomposing properties after having absorbed water can be obtained, and they completed the present invention.

Specifically, the present invention includes, for example, the inventions described in the following items.

Item 1

A water-absorbent resin having such a structure that a polymer formed from a water-soluble ethylenically unsaturated monomer is crosslinked by using a post-crosslinking agent, wherein the water-absorbent resin has:

(1) a water-retention capacity for physiological saline of 35 g/g or more,
(2) a water-absorption capacity for physiological saline under a load of 4.14 kPa of 10 mL/g or more,
(3) an initial gel viscosity of 3000 mPa·s or more, and
(4) a gel decomposition index represented by formula (I) of 0.60 or less, $$\text{gel decomposition index} = B/A \qquad \text{formula (I):}$$

wherein A represents an initial gel viscosity (mPa's), and B represents a gel viscosity after one day (mPa·s).

Item 2

The water-absorbent resin according to Item 1, wherein the polymer is formed by reversed-phase suspension polymerization of the water-soluble ethylenically unsaturated monomer.

Item 3

An absorbent article comprising an absorbent material that contains the water-absorbent resin of Item 1 or 2.

Advantageous Effects of Invention

The water-absorbent resin according to the present invention exhibits excellent self-decomposing properties after the resin has absorbed water. Thus, when recovering a recyclable resource containing the water-absorbent resin, the recyclable resource and the water-absorbent resin can be easily separated; thus, the recyclable resource can be recovered in a simple manner.

BRIEF DESCRIPTION OF DRAWINGS

FIG. 1 is a schematic diagram illustrating the schematic structure of a device for measuring the water-absorption capacity for physiological saline under a load of 4.14 kPa.

DESCRIPTION OF EMBODIMENTS

The following describes embodiments of the present invention in detail. In the present specification, the terms "comprise," "contain," and "include" include the concepts of comprising, containing, consisting essentially of, and consisting of.

In the present specification, the numerical range expressed as "X to Y" means a numerical range including X as the lower limit and Y as the upper limit. When multiple lower limits and multiple upper limits are described, any lower limit and any upper limit can be selected, and a specific numerical range can be set by describing the range by connecting the selected lower limit and upper limit by "to" such as "X to Y."

1. Water-Absorbent Resin

The water-absorbent resin according to the present invention has such a structure that a polymer formed from a water-soluble ethylenically unsaturated monomer is crosslinked by using a post-crosslinking agent. In particular, the water-absorbent resin according to the present invention satisfies the following requirements (1), (2), (3), and (4):
(1) the water-absorbent resin has a water-retention capacity for physiological saline of 35 g/g or more;
(2) the water-absorbent resin has a water-absorption capacity for physiological saline under a load of 4.14 kPa of 10 mL/g or more;
(3) the water-absorbent resin has an initial gel viscosity of 3000 mPa·s or more; and
(4) the water-absorbent resin has a gel decomposition index represented by formula (I) of 0.60 or less, gel decomposition index=$B/A$   formula (I):

wherein A represents an initial gel viscosity (mPa's), and B represents a gel viscosity after one day (mPa's).

The water-absorbent resin according to the present invention has a water-retention capacity for physiological saline of 35 g/g or more (i.e., the lower limit of the water-retention capacity is 35 g/g). The method for measuring the water-retention capacity is described in the Examples section in detail.

The water-absorbent resin according to the present invention has a water-retention capacity for physiological saline of 35 g/g or more (i.e., the water-absorbent resin satisfies requirement (1)); this indicates that the water-absorbent resin is excellent in water-absorption ability, and when used in an absorbent article, the water-absorbent resin can impart a better absorption ability to the absorbent article. From the standpoint of enabling the water-absorbent resin to have a better water-absorption ability, the lower limit of the water-retention capacity is preferably 40 g/g, and more preferably 45 g/g. The upper limit of the water-retention capacity may be, for example, 100 g/g, and is preferably 90 g/g, and more preferably 80 g/g.

The water-absorbent resin according to the present invention has a water-absorption capacity for physiological saline under a load of 4.14 kPa of 10 mL/g or more (i.e., the lower limit of the water-absorption capacity for physiological saline under a load of 4.14 kPa is 10 mL/g). The method for measuring the water-absorption capacity for physiological saline under a load of 4.14 kPa is described in the Examples section in detail.

The water-absorbent resin according to the present invention has a water-absorption capacity for physiological saline under a load of 4.14 kPa of 10 mL/g or more (i.e., the water-absorbent resin satisfies requirement (2)); this indicates that the absorption amount of the water-absorbent resin under a load is sufficient, which makes it easier to use the water-absorbent resin in a variety of applications. From the standpoint of enabling the water-absorbent resin to have a better water-absorption ability, the lower limit of the water-absorption capacity for physiological saline under a load of 4.14 kPa is preferably 13 mL/g, and more preferably 15 mL/g. The upper limit of the water-absorption capacity for physiological saline under a load of 4.14 kPa may be, for example, 40 mL/g, and is preferably 35 mL/g, and more preferably 30 mL/g.

The water-absorbent resin according to the present invention has an initial gel viscosity of 3000 mPa·s or more (i.e., the lower limit of the initial gel viscosity is 3000 mPa's). The method for measuring the initial gel viscosity is described in the Examples section in detail.

The water-absorbent resin according to the present invention has an initial gel viscosity of 3000 mPa s or more (i.e., the water-absorbent resin satisfies requirement (3)); thus, it makes it easier to produce an absorbent article with excellent usability and better absorption ability. From this standpoint, the lower limit of the initial gel viscosity is preferably 3500 mPa·s, and more preferably 4000 mPa·s. The upper limit of the initial gel viscosity may be, for example, 20000 mPa·s, and is preferably 15000 mPa·s, more preferably 13000 mPa·s, and still more preferably 9000 mPa·s.

The water-absorbent resin according to the present invention has a gel decomposition index of 0.60 or less (i.e., the upper limit of the gel decomposition index is 0.60). The method for measuring the gel decomposition index is described in the Examples section in detail.

The water-absorbent resin according to the present invention has a gel decomposition index represented by formula (I) of 0.60 or less (i.e., the water-absorbent resin satisfies requirement (4)); thus, the water-absorbent resin rapidly decomposes after the resin has absorbed water (the water-absorbent resin has excellent self-decomposing properties). Articles containing this water-absorbent resin, such as absorbent articles, are easy to recycle and dispose of, and are preferable from the viewpoint of eco-friendliness. The upper limit of the gel decomposition index is preferably 0.55, and more preferably 0.50. The lower limit of the gel decomposition index is, for example, 0.01, and preferably 0.1.

The water-absorbent resin according to the present invention has such a structure that a polymer formed from a water-soluble ethylenically unsaturated monomer (simply "polymer" below) is crosslinked by using a post-crosslinking agent. Due to its structure crosslinked using a post-crosslinking agent, the water-absorbent resin has a high crosslink density near its surface.

The inside of the polymer has a crosslinked structure. This internal crosslinked structure is formed when a water-soluble ethylenically unsaturated monomer is polymerized. The crosslink density of this crosslinked structure can be increased by using the same crosslinking agent as that of the post-crosslinking agent mentioned above or a crosslinking agent different from the post-crosslinking agent when polymerizing a water-soluble unsaturated monomer. Below, the crosslinking agent for use in crosslinking the inside of the polymer is referred to as an "internal crosslinking agent" to distinguish it from the post-crosslinking agent. Examples of usable internal crosslinking agents are described later in detail in the "2. A Method for Producing Water-absorbent Resin" section.

The water-soluble ethylenically unsaturated monomer for use is, for example, selected from a wide range of known monomers usable in typical water-absorbent resins. Examples of the water-soluble ethylenically unsaturated monomer include (meth)acrylic acid (in this specification, "acrylic" and "methacrylic" are together referred to as "(meth)acrylic"; the same applies below) and salts thereof; 2-(meth)acrylamide-2-methylpropanesulfonic acid and salts thereof; nonionic monomers, such as (meth)acrylamide, N,N-dimethyl (meth)acrylamide, 2-hydroxyethyl (meth) acrylate, N-methylol (meth)acrylamide, and polyethylene glycol mono(meth)acrylate; and amino group-containing unsaturated monomers, such as N,N-diethylaminoethyl (meth)acrylate, N,N-diethylaminopropyl (meth)acrylate, and diethylaminopropyl (meth)acrylamide, and quaternized products thereof. These water-soluble ethylenically unsaturated monomers may be used singly or (copolymerized) in a combination of two or more. In particular, from the standpoint of convenience in industrial availability, (meth) acrylic acid and salts thereof, (meth)acrylamide, and N,N-dimethyl acrylamide are preferable, and (meth)acrylic acid and salts thereof are more preferable.

When using acrylic acid and salts thereof as these water-soluble ethylenically unsaturated monomers, it is preferable to use 70 to 100 mol % of acrylic acid and salts thereof, as the main water-soluble ethylenically unsaturated monomers, of the total water-soluble ethylenically unsaturated monomers.

When the water-soluble ethylenically unsaturated monomer described above is subjected to reversed-phase suspension polymerization, the monomer for use may be prepared in the form of an aqueous solution in order to increase the dispersion efficiency in a hydrocarbon dispersion medium. The concentration of the monomer in such an aqueous solution can be any concentration, but is typically 20 mass-or more and the saturated concentration or less, preferably 25 to 70 mass %, and more preferably 30 to 55 mass %.

When the water-soluble ethylenically unsaturated monomer has an acid group, like (meth)acrylic acid or 2-(meth) acrylamide-2-methylpropanesulfonic acid, the acid group of the water-soluble ethylenically unsaturated monomer for use may be neutralized with an alkaline neutralizer beforehand as necessary. Such an alkaline neutralizer can be any alkaline neutralizer, and examples include alkali metal salts, such as sodium hydroxide, sodium carbonate, sodium hydrogen carbonate, potassium hydroxide, and potassium carbonate; and ammonia. In particular, these alkaline neutralizers may be prepared in the form of an aqueous solution in order to simplify the neutralization operation. These alkaline neutralizers may be used singly or in a combination of two or more.

The degree of neutralization of the water-soluble ethylenically unsaturated monomer with an alkaline neutralizer can be any degree. In order to increase the water-absorption ability by increasing the osmotic pressure of the water-absorbent resin and to avoid safety problems that may arise due to the presence of excessive alkaline neutralizer, the degree of neutralization is typically preferably 10 to 100 mol %, and more preferably 30 to 80 mol % of all acid groups in the water-soluble ethylenically unsaturated monomer.

The type of the post-crosslinking agent can be selected, for example, from a wide range of known post-crosslinking agents usable in water-absorbent resins. The post-crosslinking agent for use can be a compound having two or more reactive functional groups. Specific examples of the post-crosslinking agent include polyols, such as ethylene glycol, propylene glycol, 1,4-butanediol, trimethylolpropane, glycerol, polyoxyethylene glycol, polyoxy propylene glycol, and polyglycerol; polyglycidyl compounds, such as (poly)ethylene glycol diglycidyl ether, (poly)glycerol diglycidyl ether, (poly)glycerol triglycidyl ether, trimethylolpropane triglycidyl ether, (poly)propylene glycol polyglycidyl ether, and (poly)glycerol polyglycidyl ether; halo epoxy compounds, such as epichlorohydrin, epibromohydrin, and α-methyl epichlorohydrin; isocyanate compounds, such as 2,4-tolylene diisocyanate, and hexamethylene diisocyanate; oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds, such as 1,2-ethylene bis oxazoline; carbonate compounds, such as ethylene carbonate; and hydroxy alkyl amide compounds, such as bis[N,N-di(β-hydroxyethyl)]adipamide. Of these, polyglycidyl compounds, such as (poly)ethylene glycol diglycidyl ether, (poly)ethylene glycol triglycidyl ether, (poly)glycerol diglycidyl ether, (poly)glycerol triglycidyl ether, (poly)propylene glycol polyglycidyl ether, and (poly) glycerol polyglycidyl ether are particularly preferable. These post-crosslinking agents may be used singly or in a combination of two or more.

The water-absorbent resin according to the present invention has a median particle size of, for example, 100 to 1000 μm, preferably 200 to 800 μm, more preferably 250 to 600 μm, and still more preferably 300 to 500 μm.

The shape of the water-absorbent resin according to the present invention may be any of a variety of shapes, such as spheres, powder, granules, ellipses, flakes, rods, and chunks.

The water-absorption speed at which the water-absorbent resin according to the present invention absorbs physiological saline is, for example, 30 seconds or more, preferably 50 seconds or more, and more preferably 70 seconds or more. The method for measuring the water-absorption speed is described in the Examples section in detail.

2. A Method for Producing Water-Absorbent Resin

The water-absorbent resin according to the present invention can be produced, for example, by a method including the steps of polymerizing a water-soluble ethylenically unsaturated monomer to prepare a polymer (polymerization step), removing water from the polymer (drying step), and treating the polymer with a post-crosslinking agent (post-crosslinking step). The following describes the method for producing the water-absorbent resin according to the present invention in detail.

Polymerization Step

The polymerization step is for polymerizing a water-soluble ethylenically unsaturated monomer to obtain a polymer. The polymerization method can be any method, and examples include reversed-phase suspension polymerization, aqueous solution polymerization, and emulsion polymerization. It is preferable to use reversed-phase suspension polymerization taking into consideration simplicity of the production steps, ease of obtaining a water-absorbent resin with an excellent water-absorption ability, and ease of satisfying requirements (1) to (4) described above.

The reversed-phase suspension polymerization refers to, for example, a method in which a poorly soluble monomer is suspended in a dispersion medium in the presence of a dispersion stabilizer and polymerized.

The dispersion medium for use in reversed-phase suspension polymerization may be a hydrocarbon dispersion medium. The hydrocarbon dispersion medium includes aliphatic hydrocarbons, such as n-hexane, n-heptane, n-octane, and ligroin; alicyclic hydrocarbons, such as cyclopentane, methyl cyclopentane, cyclohexane, and methyl cyclohexane; and aromatic hydrocarbons, such as benzene, toluene, and xylene. Of these dispersion mediums, from the standpoint of convenience in industrial availability, quality stability, and low price, n-hexane, n-heptane, and cyclohexane are preferably used. These dispersion mediums may be used singly or in a combination of two or more. Examples of usable dispersion mediums include Exxsol Heptane (Exxon Mobil Corporation: heptane and isomeric hydrocarbons) and Nappar6 (Exxon Mobil Corporation: cyclohexane and isomeric hydrocarbons), which are known as combined solvents.

The water-soluble ethylenically unsaturated monomer usable in reversed-phase suspension polymerization is the same as those described in the "1. Water-absorbent Resin" section.

In reversed-phase suspension polymerization, a thickening agent may be used as necessary. Examples of the thickening agent for use include hydroxyethyl cellulose, hydroxypropyl cellulose, methylcellulose, carboxy methylcellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, and polyethylene oxide.

The dispersion stabilizer for use in reversed-phase suspension polymerization may be a surfactant. Examples include sucrose fatty acid esters, polyglycerol fatty acid esters, sorbitan fatty acid esters, polyoxyethylene sorbitan fatty acid esters, polyoxyethylene glycerol fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, polyethylene glycol fatty acid esters, alkyl glucoside, N-alkyl gluconamide, polyoxyethylene fatty acid amide, polyoxyethylene alkylamine, phosphoric esters of polyoxyethylene alkyl ethers, and phosphoric esters of polyoxyethylene alkyl allyl ethers. Of these, from the standpoint of monomer dispersion stability, for example, sorbitol fatty acid esters, polyglycerol fatty acid esters, and sucrose fatty acid esters are preferable. These surfactants may be used singly or in a combination of two or more.

The amount of the surfactant for use is preferably 0.1 to 30 parts by mass, and more preferably 0.3 to 20 parts by mass, per 100 parts by mass of the water-soluble ethylenically unsaturated monomer in the first stage, in order to keep the water-soluble ethylenically unsaturated monomer well dispersed in a hydrocarbon dispersion medium and to achieve a dispersion effect that matches the amount of the used surfactant.

The dispersion stabilizer for use may be a combination of a surfactant with a polymeric dispersant. Usable polymeric dispersants include maleic anhydride-modified polyethylene, maleic anhydride-modified polypropylene, maleic anhydride-modified ethylene-propylene copolymers, maleic anhydride-modified EPDM (ethylene-propylene-diene terpolymer), maleic anhydride-modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, and ethyl hydroxyethyl cellulose. Of these, from the standpoint of monomer dispersion stability, for example, maleic anhydride-modified polyethylene, maleic anhydride-modified polypropylene, maleic anhydride-modified ethylene-propylene copolymers, maleic anhydride-ethylene copolymers, maleic anhydride-propylene copolymers, maleic anhydride-ethylene-propylene copolymers, polyethylene, polypropylene, ethylene-propylene copolymers, oxidized polyethylene, oxidized polypropylene, and oxidized ethylene-propylene copolymers are preferable. These polymeric dispersants may be used singly or in a combination of two or more.

The amount of the polymeric dispersant for use is preferably 0.1 to 30 parts by mass, and more preferably 0.3 to 20 parts by mass, per 100 parts by mass of the water-soluble ethylenically unsaturated monomer in the first stage, in order to keep the water-soluble ethylenically unsaturated monomer well dispersed in a hydrocarbon dispersion medium and to achieve a dispersion effect that matches the amount of the used polymeric dispersant.

In the polymerization step, for example, a wide range of known polymerization initiators can be used. Examples of radical polymerization initiators include persulfates, such as potassium persulfate, ammonium persulfate, and sodium persulfate; peroxides, such as methyl ethyl ketone peroxide, methyl isobutyl ketone peroxide, di-t-butylperoxide, t-butyl cumylperoxide, and hydrogen peroxide; and azo compounds, such as 2,2'-azobis(2-methylpropionamidine)dihydrochloride, 2,2'-azobis[2-(N-phenylamidino)propane]dihydrochloride, 2,2'-azobis[2-(N-allylamidino)propane]dihydrochloride, and 4,4'-azobis(4-cyanovaleric acid).

These radical polymerization initiators may be used singly; however, from the standpoint of the ease of satisfying requirements (1) to (4) described above, it is preferable to use the radical polymerization initiators in a combination of two or more. For example, a persulfate, such as potassium persulfate, and an azo compound, such as 2,2'-azobis(2-amidinopropane)dihydrochloride, can be used in a combination. The radical polymerization initiators can also be combined with a reducing agent, such as sodium sulfite, sodium hydrogen sulfite, ferrous sulfate, and L-ascorbic acid, to use them as redox polymerization initiators.

The lower limit of the amount of the radical polymerization initiator for use in the polymerization step is, for example, preferably 0.01 mmol, and more preferably 0.05 mmol, per mol of the water-soluble ethylenically unsaturated monomer for use. The upper limit of the amount of the radical polymerization initiator for use is preferably 20 mmol, and more preferably 10 mmol, per mol of the water-soluble ethylenically unsaturated monomer for use. The use of the radical polymerization initiator in an amount within these numerical ranges makes it easier to satisfy requirements (1) to (4) described above.

In the polymerization step, a chain transfer agent may optionally be used. Examples of the chain transfer agent include hypophosphites, thiols, thiolic acids, secondary alcohols, and amines.

In the polymerization step, an internal crosslinking agent may optionally be used. The internal crosslinking agent includes compounds having two or more polymerizable unsaturated groups. Specific examples of the internal crosslinking agent include di or tri(meth)acrylic acid esters of polyols, such as (poly)ethylene glycol (in the present specification, for example, "polyethylene glycol" and "ethylene glycol" together are referred to as "(poly)ethylene glycol"; the same applies below), (poly)propylene glycol, trimethylolpropane, glycerol polyoxyethylene glycol, polyoxy propylene glycol, and (poly)glycerol; unsaturated polyesters obtained by reacting the polyols listed above with unsaturated acids, such as maleic acid and fumaric acid; bis acrylamides, such as N,N'-methylene bis (meth)acrylamide; di or tri(meth)acrylic acid esters obtained by reacting polyepoxide with (meth)acrylic acid; di(meth)acrylic acid carbamyl esters obtained by reacting polyisocyanate, such as tolylene diisocyanate and hexamethylene diisocyanate, with hydroxyethyl (meth)acrylate; allylated starch; allylated cellulose; diallyl phthalate; N,N',N''-triallyl isocyanurate; and divinyl benzene.

The internal crosslinking agent also includes, in addition to the compounds having two or more polymerizable unsaturated groups, glycidyl group-containing compounds, such as (poly)ethylene glycol diglycidyl ether, (poly)propylene glycol diglycidyl ether, and (poly)glycerol diglycidyl ether, (poly)ethylene glycol, (poly)propylene glycol, (poly)glycerol, pentaerythritol, ethylene diamine, polyethyleneimine, and glycidyl (meth)acrylate. These internal crosslinking agents may be used in a combination of two or more. Of these, from the standpoint of excellent reactivity at low temperatures, (poly)ethylene glycol diglycidyl ether, (poly)propylene glycol diglycidyl ether, (poly)glycerol diglycidyl ether, and N,N'-methylene bis acrylamide are preferable.

The lower limit of the amount of the internal crosslinking agent for use is preferably 0.0001 mol, more preferably 0.0005 mmol, still more preferably 0.001 mmol, and particularly preferably 0.01 mmol, per mol of the water-soluble ethylenically unsaturated monomer for use from the standpoint of the ease of satisfying requirements (1) to (4) described above. The upper limit of the amount of the internal crosslinking agent for use is preferably 5 mmol, more preferably 0.5 mmol, and still more preferably 0.05 mmol, per mol of the water-soluble ethylenically unsaturated monomer for use.

The temperature for the polymerization reaction can be suitably determined in accordance with the type and the amount of the radical polymerization initiator, for example. The temperature for the polymerization reaction may be, for example, 20 to 110° C., and preferably 40 to 90° C. The reaction time can be set, for example, within the range of 0.1 hours to 4 hours.

The polymerization step in reversed-phase suspension polymerization can be performed, for example, by adding an aqueous solution containing an optionally neutralized water-soluble ethylenically unsaturated monomer, a thickening agent, a radical polymerization initiator, and an internal crosslinking agent to a dispersion medium in which a polymer dispersion stabilizer is dispersed, and then adding a surfactant to form a suspension. The order of adding each starting material is not limited to this order.

The water-soluble ethylenically unsaturated monomer is polymerized, thereby forming a polymer. For example, reversed-phase suspension polymerization provides a slurry in which the polymer formed from the water-soluble ethylenically unsaturated monomer is dispersed.

The reversed-phase suspension polymerization may be performed in one stage, or in multiple stages such as two or more stages. The number of stages is preferably two or three from the standpoint of increasing productivity.

In reversed-phase suspension polymerization performed in two or more stages, for example, the first stage of reversed-phase suspension polymerization is performed by the method described above, and then the water-soluble ethylenically unsaturated monomer is added to and mixed with the reaction mixture obtained in the first stage of the polymerization step, followed by performing the second and following stages of reversed-phase suspension polymerization in the same manner as in the first stage. In each subsequent stage after the second stage of reversed-phase suspension polymerization, the radical polymerization initiator and the optionally added internal crosslinking agent, in addition to the water-soluble ethylenically unsaturated monomer, can be added in a molar ratio of each component to the water-soluble ethylenically unsaturated monomer within the numerical ranges described, based on the amount of the water-soluble ethylenically unsaturated monomer added in each stage after the second stage of reversed-phase suspension polymerization; and then reversed-phase suspension polymerization can be performed under the same conditions as those of the method described above.

When performing reversed-phase suspension polymerization in multiple stages, it is preferable to set the total amount of the polymerization initiator and the total amount of the internal crosslinking agent, per mol of the water-soluble ethylenically unsaturated monomer used in reversed-phase suspension polymerization, so as to fall within the numerical ranges described above, from the standpoint of the ease of satisfying requirements (1) to (4) described above.

Drying Step

The drying step is for removing water from the polymer obtained in the polymerization step by adding energy such as heat from outside to the polymer. For example, in the case of reversed-phase suspension polymerization, water, the hydrocarbon dispersion medium, and other components can be removed from the polymer by performing azeotropic distillation in the drying step, with the polymer (hydrogel) obtained in the polymerization step being dispersed in the hydrocarbon dispersion medium. The drying step may be performed under ordinary pressure or under reduced pressure, and may be performed in a gas stream such as nitrogen in order to increase drying efficiency. When the drying step is performed under ordinary pressure, the drying temperature is preferably 70 to 250° C., more preferably 80 to 180° C., still more preferably 80 to 140° C., and particularly preferably 90 to 130° C. Under reduced pressure, the drying temperature is preferably 40 to 160° C., and more preferably 50 to 120° C. The water content of the polymer before the post-crosslinking step described below can be adjusted by performing the drying step. The drying step may be performed concurrently with the post-crosslinking step described below.

Post-Crosslinking Step

The post-crosslinking step is for treating the polymer formed from the water-soluble ethylenically unsaturated monomer obtained in the polymerization step with a post-crosslinking agent. Examples of the type of the post-crosslinking agent are those of the post-crosslinking agent listed in the "1. Water-absorbent Resin" section.

The method for treating the polymer with a post-crosslinking agent is, for example, as follows: a post-crosslinking agent and a solvent are mixed to prepare a treatment solution containing the post-crosslinking agent, and this treatment solution is brought into contact with the polymer to treat the polymer with the post-crosslinking agent.

The solvent for use in preparing the treatment solution containing a post-crosslinking agent can be any solvent. For example, hydrophilic organic solvents that dissolve the post-crosslinking agent well can be used. The solvent includes, in addition to water, lower alcohols, such as methyl alcohol, ethyl alcohol, n-propyl alcohol, isopropyl alcohol, and propylene glycol; ketones, such as acetone, and methyl ethyl ketone; ethers, such as diethyl ether, dioxane, and tetrahydrofuran; amides, such as N,N-dimethyl formamide; and sulfoxides, such as dimethyl sulfoxide. These hydrophilic organic solvents each may be used singly or in a combination of two or more, or as a mixture solvent with water.

The treatment solution can be prepared, for example, by dissolving the post-crosslinking agent in a solvent. The mixture ratio of the post-crosslinking agent to the solvent can be any ratio. For example, the post-crosslinking agent is added in an amount of 0.1 to 10 parts by mass, per 100 parts by mass of the solvent.

The contact of the polymer with the treatment solution can be performed, for example, by mixing the polymer with the treatment solution by a suitable method. For example, the following method can be used: the treatment solution is added to the polymer in a container with the polymer immobile or with the polymer being stirred in a hydrocarbon dispersion medium.

From the standpoint of the ease of satisfying requirements (1) to (4) described above, the lower limit of the amount of the post-crosslinking agent for use is preferably 0.01 mmol, more preferably 0.05 mmol, and still more preferably 0.1 mmol, per mol of the water-soluble ethylenically unsaturated monomer that constitutes the polymer to be post-crosslinked. The upper limit of the amount of the post-crosslinking agent for use is preferably 10 mmol, more preferably 5 mmol, and still more preferably 2 mmol, per mol of the water-soluble ethylenically unsaturated monomer.

From the standpoint of the ease of satisfying requirements (1) to (4) described above, it is preferable to add the post-crosslinking agent to a polymer with a low water content. Specifically, it is preferable to add the post-crosslinking agent to the polymer, with the polymer containing less than 100 mass % of water, more preferably 50 mass % or less of water, and still more preferably 10 mass % or less of water. The water content of the polymer refers to a percentage of water contained in the polymer immediately before the post-crosslinking agent is added. The method for measuring the water content is described in the Examples below.

The lower limit of the water content of the polymer can be any content. The lower limit is preferably 0.01 mass %, more preferably 0.05 mass %, and still more preferably 0.1 mass %. The water content of the polymer is adjustable by the drying step described above.

The reaction temperature in the post-crosslinking step (i.e., the temperature at which the polymer is treated with the post-crosslinking agent) is preferably 50 to 250° C., more preferably 60 to 180° C., and still more preferably 60 to 140° C. The reaction time for the post-crosslinking (i.e., the time period during which the polymer is treated with the post-crosslinking agent at the reaction temperature) cannot be generalized due to the difference in the reaction temperature, type and amount of the post-crosslinking agent etc. However, the reaction time is typically 1 to 300 minutes, and preferably 5 to 200 minutes.

In the steps after the polymerization step, additives according to the purpose may be added in order to impart various properties to the water-absorbent resin. Such additives include inorganic powders, surfactants, oxidants, reducing agents, metal chelating agents, radical chain inhibitors, antioxidants, antimicrobial agents, and deodorants. For example, 0.05 to 5 parts by mass of amorphous silica (inorganic powder) per 100 parts by weight of the water-absorbent resin may be added to improve the fluidity of the water-absorbent resin.

3. Absorbent Article

The absorbent material containing the water-absorbent resin according to the present invention is formed from the water-absorbent resin and hydrophilic fibers. Examples of the structure of the absorbent material include a mixture dispersion obtained by mixing the water-absorbent resin with hydrophilic fibers so as to form a homogeneous composition, a sandwich structure in which the water-absorbent resin is sandwiched between the layers of hydrophilic fibers, and a structure in which the water-absorbent resin and hydrophilic fibers are wrapped in tissue. However, the present invention is not limited to these examples of the structure.

Other components, such as an adhesive binder for increasing the shape retention properties of the absorbent material (e.g., thermally adhesive synthetic fibers, a hot-melt adhesive, and an adhesive emulsion) may be added to the absorbent material.

Examples of hydrophilic fibers include cellulose fibers, such as cotton-like pulp obtained from wood, mechanical pulp, chemical pulp, and semi-chemical pulp; artificial cellulose fibers, such as rayon, and acetate; and fibers composed of synthetic resins, such as hydrophilized polyamide, polyester, and polyolefin.

The absorbent article can be prepared by holding the absorbent material of the present invention described above between a liquid-permeable sheet (top sheet) through which liquid can permeate and a liquid-impermeable sheet (back sheet) through which liquid cannot permeate. The liquid-permeable sheet is disposed on the side that comes into contact with the body, and the liquid-impermeable sheet is disposed on the side opposite the side that comes into contact with the body.

Examples of the liquid-permeable sheet include air-through, spun-bonded, chemical-bonded, or needle-punched non-woven fabrics and porous synthetic resin sheets that are formed of fibers, such as polyethylene, polypropylene, or polyester.

Examples of the liquid-impermeable sheet include synthetic resin films composed of resin, such as polyethylene, polypropylene, or polyvinyl chloride.

The type of the absorbent article can be any type. Examples include hygiene materials, such as disposable diapers, sanitary napkins, and incontinence pads; urine absorbers for pets; civil engineering and construction materials, such as packing materials; food freshness-maintaining materials, such as drip absorbers, and refrigerants; agriculture and horticulture materials, such as water retention materials for soil; and waterproof materials.

EXAMPLES

The following describes the present invention in more detail with reference to Examples. However, the present invention is not limited to embodiments of these Examples.

Example 1

Production of Polymer Formed from Water-Soluble Ethylenically Unsaturated Monomer by Reversed-Phase Suspension Polymerization A 2-L round-bottom cylindrical separable flask with an inner diameter 110 mm, equipped with a reflux condenser, a dropping funnel, a nitrogen-gas inlet tube, and stirring blades (two sets of 4 slanted paddle blades with a blade diameter of 50 mm) was prepared. As a hydrocarbon dispersion medium, 300 g of n-heptane was placed in this flask, and 0.74 g of sucrose stearate (Mitsubishi-Kagaku Foods Corporation, RYOTO Sugar Ester S-370) and 0.74 g of a maleic anhydride-modified ethylene-propylene copolymer (Mitsui Chemicals, Inc., Hi-WAX 1105A) were added thereto. The mixture was heated with stirring and dissolved, and then cooled to 55° C.

92 g (1.02 mol) of an 80 mass % acrylic acid aqueous solution was placed in a 500-mL Erlenmeyer flask, and 102.2 g of a 30 mass % sodium hydroxide aqueous solution was added dropwise with cooling from outside to neutralize 75 mol % of the acrylic acid aqueous solution. 0.092 g of hydroxyl ethyl cellulose (Sumitomo Seika Chemicals Co., Ltd, HEC AW-15F) as a thickening agent, 0.055 g (0.204 mmol) of 2,2'-azobis(2-amidinopropane)dihydrochloride as an azo compound, 0.009 g (0.034 mmol) of potassium persulfate as a persulfate, 0.005 g (0.026 mmol) of ethylene glycol diglycidyl ether as an internal crosslinking agent, and 48.0 g of ion-exchanged water were added thereto and dissolved, thereby preparing a monomer aqueous solution for the polymerization step in the first stage.

The monomer aqueous solution was added to the separable flask, and the inside of the system (a container in which the reaction proceeds; the same applied below) was fully replaced with nitrogen. The flask was immersed in a water bath at 70° C., and heated, followed by performing a polymerization reaction for 10 minutes, thereby preparing a reaction mixture in the first stage.

128.8 g (1.43 mol) of an 80 mass % acrylic acid aqueous solution was placed in another 500-mL Erlenmeyer flask, and 143.1 g of a 30 mass % sodium hydroxide aqueous solution was added dropwise thereto with cooling from outside to neutralize 75 mol % of the acrylic acid aqueous solution. 0.077 g (0.285 mmol) of 2,2'-azobis(2-amidinopropane)dihydrochloride as an azo compound, 0.013 g (0.048 mmol) of potassium persulfate as a peroxide, 0.012 g (0.069 mmol) of ethylene glycol diglycidyl ether as an internal crosslinking agent, and 12.5 g of ion-exchanged water were added thereto and dissolved, thereby preparing a monomer aqueous solution for the polymerization step in the second stage. The reaction mixture in the first stage was cooled to 25° C., and then the entire monomer aqueous solution in the second stage was added to the reaction mixture in the first stage, followed by maintaining the mixture at 25° C. for 30 minutes while replacing the inside of the system with nitrogen. Thereafter, the flask was immersed in a water bath at 70° C. again, and heated, followed by a polymerization reaction in the second stage for 5 minutes, thereby preparing a reaction mixture in the second stage.

The ethylenically unsaturated monomer (acrylic acid) used in the polymerization steps of the first stage and the second stage was 2.45 mmol in total. The internal crosslinking agent (ethylene glycol diglycidyl ether) used in the polymerization steps of the first stage and the second stage was 0.017 g (0.095 mmol) in total. The amount of the internal crosslinking agent was 0.0388 mmol relative to 1 mol of the ethylenically unsaturated monomer (acrylic acid) used in the polymerization steps of the first stage and the second stage.

The reaction mixture in the second stage was heated in an oil bath at 125° C. While n-heptane was refluxed by azeotropic distillation of n-heptane and water, 255 g of water was removed outside the system. As a chelating agent, 5.89 g (0.53 mmol) of a 4.5% aqueous solution of a diethylenetriaminepentaacetic acid pentasodium salt was added, followed by evaporating n-heptane, thereby obtaining a polymer. The obtained polymer was passed through a sieve with an opening of 850 μm, thereby obtaining 236.6 g of a polymer in the form of secondary particles that are aggregates of spherical particles.

Post-Crosslinking Step

Subsequently, 10 g of propylene glycol, 30 g of ion-exchanged water, 10 g of isopropanol, and 0.5 g (2.87 mmol) of ethylene glycol diglycidyl ether as a post-crosslinking agent were added to a 100-mL beaker, and the mixture was stirred for 5 minutes with a magnetic stirrer bar (with no ring of 8-mm diameter×30 mm), thereby preparing 50.5 g of treatment solution containing the post-crosslinking agent.

30 g of the polymer was placed in a 2-L round-bottom cylindrical separable flask with an inner diameter of 110 mm, equipped with a stirring blade (blade diameter: 90 mm), which was made of fluorine resin in an anchor shape. While the polymer was stirred at 500 rpm, 1.12 g of the treatment solution (containing 0.0636 mmol of ethylene glycol diglycidyl ether, which is a post-crosslinking agent) was added dropwise to the separable flask. With the water content of the polymer being 8%, the post-crosslinking agent was added to the flask. The method for measuring the water content is described in detail in the following section. The amount of the post-crosslinking agent was 0.21 mmol relative to 1 mol of the ethylenically unsaturated monomer (acrylic acid) that constitutes the polymer to be post-crosslinked. After stirring for 1 minute from the completion of dropwise addition, the polymer was taken out. The polymer was spread in a fluorine resin-coated tray (bottom surface: 26×20 cm, depth: about 5 cm), and the tray was allowed to stand in a hot-air dryer (Advantec, FV-320) set at 180° C. for 40 minutes. This caused the polymer to become crosslinked by the post-crosslinking agent (reaction temperature in the post-crosslinking step: 180° C., reaction time: 40 minutes), thereby obtaining a target water-absorbent resin. The obtained water-absorbent resin was mixed with amorphous silica (Evonik Degussa Japan Co., Ltd., Carplex #80) in an amount of 0.2 mass % based on the water-absorbent resin, and the resulting water-absorbent resin was evaluated in accordance with the following test methods.

Measurement of Water Content About 2 g of the polymer was precisely weighed in a pre-weighed aluminum foil container (No. 8) ($W_A$ (g)). The sample was dried for 2 hours in a hot-air dryer (Advantec, FV-320) at an internal temperature set to 105° C., and then cooled in a desiccator, followed by measuring the mass of the dried polymer $W_E$ (g). The water content of the polymer was calculated from the following equation.

$$\text{water content (\%)} = \{[W_A - W_B]/W_A\} \times 100$$

Example 2

The procedure of Example 1 was repeated except that the amount of the treatment solution containing the post-crosslinking agent in the post-crosslinking step was changed to 3.36 g (containing 0.191 mmol of ethylene glycol diglycidyl ether, which is a post-crosslinking agent), thereby obtaining a water-absorbent resin. The amount of the post-crosslinking agent in the post-crosslinking step was 0.62 mmol relative to 1 mol of the used ethylenically unsaturated monomer (acrylic acid).

Example 3

The procedure of Example 1 was repeated except that the amount of the treatment solution containing the post-crosslinking agent in the post-crosslinking step was changed to 6.72 g (containing 0.382 mmol of ethylene glycol diglycidyl ether, which is a post-crosslinking agent), thereby obtaining a water-absorbent resin. The amount of the post-crosslinking agent in the post-crosslinking step was 1.24 mmol relative to 1 mol of the ethylenically unsaturated monomer (acrylic acid) that constitutes the polymer to be post-crosslinked.

Comparative Example 1

With the polymer having a high water content, the post-crosslinking agent was added. Specifically, in reversed-phase suspension polymerization, the procedure of Example 1 was repeated except that the amount of ethylene glycol diglycidyl ether for preparing the monomer aqueous solution for the polymerization step in the first stage was changed from 0.005 g to 0.012 g (0.069 mmol), thereby obtaining a reaction mixture in the second stage. The amount of the internal crosslinking agent (ethylene glycol diglycidyl ether) used in the polymerization steps of the first stage and the second stage was 0.024 g (0.138 mmol) in total. The amount of the internal crosslinking agent was 0.056 mmol relative to 1 mol of the ethylenically unsaturated monomer (acrylic acid) used in the first stage and the second stage.

The obtained reaction mixture in the second stage was heated in an oil bath at 125° C. While n-heptane was refluxed by azeotropic distillation of n-heptane and water, 255 g of water was removed to outside the system. Subsequently, 5.89 g (0.53 mmol) of a 4.5% aqueous solution of a diethylenetriaminepentaacetic acid pentasodium salt as a chelating agent and 4.42 g (0.51 mmol) of a 2% aqueous solution of ethylene glycol diglycidyl ether as a post-crosslinking agent were added to the polymer, followed by maintaining the mixture at 80° C. for 2 hours. The post-crosslinking agent was added with the water content of the polymer being 23%. The amount of the post-crosslinking agent was 0.21 mmol, relative to 1 mol of the ethylenically unsaturated monomer (acrylic acid) that constitutes the polymer to be post-crosslinked. Thereafter, n-heptane was evaporated, thereby obtaining a polymer. The obtained polymer was passed through a sieve with an opening of 850 μm, thereby obtaining 236.6 g of a water-absorbent resin in the form of aggregates of spherical particles. The obtained water-absorbent resin was mixed with amorphous silica (Evonik Degussa Japan Co., Ltd., Carplex #80) in an amount of 0.2 mass % based on the obtained water-absorbent resin, and the obtained water-absorbent resin was evaluated in accordance with the following test methods.

Comparative Example 2

One type of polymerization initiator was used. Specifically, the procedure of Example 1 was repeated except that the polymerization initiator for use in the polymerization step in the first stage was changed to 0.074 g (0.272 mmol) of potassium persulfate, and the polymerization initiator for use in the polymerization step in the second stage was changed to 0.103 g (0.381 mmol) of potassium persulfate, thereby obtaining a water-absorbent resin.

Comparative Example 3

One type of polymerization initiator was used, and a post-crosslinking agent was added with the polymer having a high water content. Specifically, the procedure of Comparative Example 1 was repeated except that the polymerization initiator for use in the polymerization step in the first stage was changed to 0.074 g (0.272 mmol) of potassium persulfate, the polymerization initiator for use in the polymerization step in the second stage was changed to 0.103 g (0.381 mmol) of potassium persulfate, and the post-crosslinking agent was added with the water content of the polymer being 20%, thereby obtaining 236.6 g of a water-absorbent resin.

Comparative Example 4

A water-absorbent resin was produced by aqueous solution polymerization. Specifically, 92 g (1.02 mol) of an 80 mass % acrylic acid aqueous solution was placed in a 2-liter five-necked, cylindrical round-bottom flask equipped with a stirrer, a stirring blade, a reflux condenser, a dropping funnel, and a nitrogen gas-inlet tube. While the flask was cooled from the outside, 102.2 g of a 30 mass % sodium hydroxide aqueous solution was added dropwise thereto to neutralize 75 mol % of the acrylic acid aqueous solution, thereby preparing a 25 mass % aqueous salt solution of partially neutralized acrylic acid.

0.013 g (0.075 mmol) of ethylene glycol diglycidyl ether as an internal crosslinking agent, and 0.055 g (0.204 mmol) of 2,2'-azobis(2-amidinopropane)dihydrochloride and 0.009 g (0.034 mmol) of potassium persulfate as a water-soluble radical polymerization initiator were added to the obtained aqueous salt solution of partially neutralized acrylic acid. The inside of the system was replaced with nitrogen gas, and the flask was maintained in a water bath at 50° C., followed by performing aqueous solution polymerization reaction for 1 hour. The amount of the internal crosslinking agent for use was 0.074 mmol, relative to 1 mol of the ethylenically unsaturated monomer (acrylic acid).

The obtained polymerization reaction product was coarsely ground with a meat grinder made of stainless steel, and dried with a hot-air dryer at 140° C. for 1 hour. Subsequently, the dried product was ground with a speed rotor mill and classified with a JIS-standard sieve (opening: 850 μm), thereby obtaining particles of 850 μm or less as a polymer of the water-soluble ethylenically unsaturated monomer (90.7 g).

In the step of post-crosslinking the obtained polymer, the procedure of the post-crosslinking step in Example 1 was repeated to post-crosslink 30 g of the polymer, except that the amount of the treatment solution containing the post-crosslinking agent was changed to 10.08 g (containing 0.573 mmol of ethylene glycol diglycidyl ether, which is a post-crosslinking agent), and that 0.75 g (0.067 mmol) of a 4.5% aqueous solution of a diethylenetriaminepentaacetic acid pentasodium salt was added as a chelating agent before the post-crosslinking agent was added in the post-crosslinking step of Example 1, thereby obtaining a water-absorbent resin. The obtained water-absorbent resin was mixed with amorphous silica (Evonik Degussa Japan Co., Ltd., Carplex #80) in an amount of 0.2 mass % based on the obtained water-absorbent resin, and the resulting water-absorbent resin was evaluated in accordance with the following test methods. The post-crosslinking agent was added with the water content of the polymer being 8%. The amount of the post-crosslinking agent added was 1.84 mmol relative to 1 mol of the ethylenically unsaturated monomer (acrylic acid) that constitutes the polymer to be post-crosslinked.

Evaluation Method

The water-absorbent resins obtained in the Examples and Comparative Examples were measured for gel viscosity (initial gel viscosity and gel viscosity after 1 day), water-retention capacity for physiological saline, water-absorption capacity for physiological saline under a load of 4.14 kPa, and water-absorption speed as described below.

Measurement of Gel Viscosity 299 g of distilled water was added to a 500-mL beaker and stirred with a magnetic stirrer bar (without a ring of 8-mm diameter×30 mm) at 600 rpm. 1.0 g of a water-absorbent resin was added into a vortex generated by stirring, and the mixture was continuously stirred until the vortex disappeared and the liquid surface turned flat. The gel viscosity of the gel that swelled to 300-fold and that was then allowed to stand at room temperature (25° C.) for 1 hour ("initial gel viscosity" of the present invention) and the gel viscosity of the gel that was allowed to stand under a hot-air dryer (Advantec, EV-320) at 90° C. for 1 day (24 hours) (gel viscosity after 1 day of the present invention) were measured with a bismetholone (Shibaura System K.K. VS-H1, rotor No. 5, rotation frequency of 20 rpm). When measuring the gel viscosity, the prepared gel was placed in a 200-mL beaker.

Measurement of Water-Retention Capacity for Physiological Saline 2.0 g of a water-absorbent resin for evaluation was placed in a cotton bag. While 500 g of physiological saline (a 0.9% sodium chloride aqueous solution) was poured into the cotton bag (cotton broadcloth No. 60, width: 100 mm, height: 200 mm), the entire resin was immersed. The upper part of the cotton bag was tied with a rubber band; after immersion for 30 minutes, the cotton bag was dehydrated for 1 minute with a dehydrator with the centrifugal force set to 167 G (Kokusan Co., Ltd., Model: H-122). The weight ($W_C$) of the cotton bag containing the swelled gel after dehydration was measured. The same procedure was performed with a cotton bag containing no sample, and the weight of the empty cotton bag ($W_D$) was measured. Then, the water-retention capacity for physiological saline was calculated in accordance with the following equation.

water–retention capacity for physiological saline (g/g)=($W_C$−$W_D$)/2.0

Measurement of Water-Absorption Capacity for Physiological Saline Under a Load of 4.14 kPa The water-absorption capacity for physiological saline under a load of 4.14 kPa of a water-absorbent resin was measured with a measurement device X, whose schematic diagram is illustrated in FIG. 1.

The measurement device X illustrated in FIG. 1 includes a burette unit 1, a pipe 2, a measurement table 3, and a measurement unit 4 placed on the measurement table 3. The burette unit 1 includes a burette 10 to the upper part of which a rubber plug 14 is connected, and to the lower part of which an air-inlet tube 11 and a cock 12 are connected, with a cock 13 provided at the upper part of the air-inlet tube 11. The pipe 2 is provided between the burette unit 1 and the measurement table 3, and the pipe 2 has a diameter of 6 mm. The measurement table 3 has a hole with a diameter of 2 mm in the middle of it, and the pipe 2 is connected to the hole. The measurement unit 4 includes a cylinder 40, a nylon mesh 41 adhered to the bottom part of the cylinder 40, and a weight 42. The cylinder 40 has an inner diameter of 2.0 cm. The nylon mesh 41 is a 200 mesh (opening: 75 μm). A predetermined amount of a water-absorbent resin 5 is to be homogeneously sprinkled across on the nylon mesh 41. The weight 42 has a diameter of 1.9 cm and a mass of 119.6 g. This weight 42 is placed on the water-absorbent resin 5, and is set to uniformly apply a load of 4.14 kPa on the water-absorbent resin 5.

In the thus-structured measurement device X, the cock 12 and the cock 13 of the burette unit 1 are first plugged, and physiological saline adjusted to 25° C. is added through the upper part of the burette 10. After the upper part of the burette is plugged with the rubber plug 14, the cock 12 and the cock 13 of the burette unit 1 are opened. Subsequently, the height of the measurement table 3 is adjusted so that the end of the pipe 2 at the center of the measurement table 3 becomes level with the air inlet of the air-inlet tube 11. At this stage, the adjustment is performed so that air of the same volume as that of physiological saline sucked out by the measurement unit is freely supplied from the air inlet.

0.10 g of the water-absorbent resin 5 is homogeneously sprinkled across on the nylon mesh 41 in the cylinder 40, and the weight 42 is placed on the water-absorbent resin 5. The measurement unit 4 is placed so that the center of the measurement unit 4 corresponds to the opening of the pipe at the center of the measurement table 3.

From the point at which the water-absorbent resin 5 starts absorbing water, the decrease in the amount of physiological saline in the burette 10 (the amount of physiological saline absorbed by the water-absorbent resin 5) $W_E$(mL) is continuously measured. The amount of water absorbed during 60 minutes from the start of absorption was determined to be the water-absorption capacity for physiological saline under a load of the water-absorbent resin 5 from the following equation.

water-absorption capacity for physiological saline under a load of 4.14 kPa (mL/g)=$W_E$/0.10

Measurement of Water-Absorption Speed (Vortex Method)

50 g of physiological saline was added to a 100-mL beaker and maintained at 25° C. in a thermostatic bath. Subsequently, 2.00 g of a water-absorbent resin was added into a vortex of the physiological saline stirred with a magnetic stirrer bar (without a ring of 8-mm diameter×30 mm) at 600 rpm, and measurement with a stopwatch was simultaneously started. The time period (seconds) until the point at which the vortex disappeared and the liquid surface turned flat (ending point) was determined to be the water-absorption speed.

TABLE 1

| | Water-retention Capacity for Physiological Saline (g/g) | Water-absorption Capacity for Physiological Saline under a Load of 4.14 kPa (mL/g) | Water-absorption Speed (second) | Gel Decomposition Index | Gel Viscosity (mPa · s) | |
|---|---|---|---|---|---|---|
| | | | | | Initial | After 1 Day |
| Example 1 | 75 | 13 | 76 | 0.34 | 8500 | 2900 |
| Example 2 | 53 | 22 | 106 | 0.40 | 7300 | 2900 |
| Example 3 | 40 | 24 | 124 | 0.50 | 5800 | 2900 |
| Comparative Example 1 | 41 | 25 | 35 | 0.70 | 8200 | 5700 |
| Comparative Example 2 | 40 | 21 | 54 | 0.68 | 11000 | 7500 |
| Comparative Example 3 | 40 | 13 | 34 | 0.90 | 9300 | 8400 |

TABLE 1-continued

|  | Water-retention Capacity for Physiological Saline (g/g) | Water-absorption Capacity for Physiological Saline under a Load of 4.14 kPa (mL/g) | Water-absorption Speed (second) | Gel Decomposition Index | Gel Viscosity (mPa·s) | |
|---|---|---|---|---|---|---|
|  |  |  |  |  | Initial | After 1 Day |
| Comparative Example 4 | 40 | 15 | 131 | 0.50 | 2000 | 1000 |

Table 1 shows the results of evaluating the evaluation samples obtained in the Examples and Comparative Examples.

The water-absorbent resins obtained in Examples 1 to 3 exhibited a significant decrease in gel viscosity after one day from the start of absorption, compared with the initial gel viscosity (the gel decomposition index is 0.60 or less in all of the cases). The results indicate that the water-absorbent resins obtained in Examples 1 to 3 have excellent self-decomposing properties. In contrast, the water-absorbent resins obtained in Comparative Examples 1 to 4 were less likely to undergo decomposition.

DESCRIPTION OF THE REFERENCE NUMERALS

X measurement device
1 burette unit
2 pipe
3 measurement table
4 measurement unit
5 water-absorbent resin particles
10 burette
11 air-inlet tube
12 cock
13 cock
14 rubber plug
40 cylinder
41 nylon mesh
42 weight

The invention claimed is:

1. A water-absorbent resin having such a structure that a polymer formed from a water-soluble ethylenically unsaturated monomer is crosslinked by using a post-crosslinking agent,
   wherein the water-absorbent resin has:
   (1) a water-retention capacity for physiological saline of 35 g/g or more,
   (2) a water-absorption capacity for physiological saline under a load of 4.14 kPa of 10 mL/g or more,
   (3) an initial gel viscosity of 3000 mPas or more, and
   (4) a gel decomposition index represented by formula (I) of 0.60 or less,
   formula (I): gel decomposition index=B/A wherein A represents an initial gel viscosity (mPas), and B represents a gel viscosity after one day (mPa·s).

2. The water-absorbent resin according to claim 1, wherein the polymer is formed by reversed-phase suspension polymerization of the water-soluble ethylenically unsaturated monomer.

3. An absorbent article comprising an absorbent material that contains the water-absorbent resin of claim 1.

4. An absorbent article comprising an absorbent material that contains the water-absorbent resin of claim 2.

* * * * *